US00PP10589P

United States Patent [19]

Halka, Jr.

[11] Patent Number: Plant 10,589

[45] Date of Patent: Sep. 8, 1998

[54] LINDEN TREE 'HALKA'

[75] Inventor: Chester J. Halka, Jr., Englishtown, N.J.

[73] Assignee: J. Frank Schmidt & Son Co., Boring, Oreg.

[21] Appl. No.: 781,672

[22] Filed: Jan. 10, 1997

[51] Int. Cl.[6] ..... A01H 5/00

[52] U.S. Cl. ..... Plt./53.4

[58] Field of Search ..... Plt./53.4

*Primary Examiner*—James R. Feyrer
*Assistant Examiner*—Kent L. Bell
*Attorney, Agent, or Firm*—Klarquist Sparkman Campbell Leigh & Whinston, LLP

[57] ABSTRACT

A linden tree named 'Halka' having a dwarf size, compact growth, and dense conical habit.

1 Drawing Sheet

DESCRIPTION

The present invention relates to a new and distinct variety of linden tree which is named 'Halka'.

I discovered my new tree as a chance seedling growing in a cultivated portion of my nursery in Englishtown, N.J. Although the parentage of my new variety is unknown, it is believed to be a chance seedling from a *Tilia cordata* tree.

As I observed the initially discovered tree of my new variety, my attention was drawn to this tree because of its dwarf size, compact growth and dense conical habit.

Observations of this tree have convinced me that it is a unique new variety.

Asexual propagation of my new tree has been performed at my direction at a J. Frank Schmidt & Son Co. nursery in Boring, Oreg., by budding onto seeding *Tilia cordata* rootstock.

This propagation, and successive asexual propagation by budding, and observation of the resulting progeny, have proven the characteristics of my new variety of linden tree to be firmly fixed. Furthermore, these observations have confirmed that my new variety represents a new and improved variety of linden tree as particularly evidenced by the unique combination of dwarf size, compact growth, and dense conical habit.

The accompanying photographs depict the color of the tree and foliage of my new variety, as well as the shape of the tree, as nearly true as is reasonably possible to make the same in a color illustration of this character.

My 'Halka' variety has not been observed under all growing conditions and thus variations may occur as a result of different growing conditions. The following is a detailed description of my new variety of linden tree with color terminology in accordance with The Royal Horticultural Society Colour Chart (R.H.S.), published by The Royal Horticultural Society of London. The observations are of trees growing in Boring, Oreg.

The Plant

Parentage: Chance seedling of unknown parentage (believed to be a chance seedling of *Tilia cordata*) found growing in a cultivated portion of my nursery in Englishtown, N.J.

Tree shape: Dwarf, compact, conical tree with densely arranged branches oriented, about a strong central leader, and extending upward at approximately 45 degrees.

Trunk: Straight, round in cross-section, sturdy, especially in relation to the dwarf overall size of the tree.

Bark: Smooth.

*Immature bark color.*—Grey-brown R.H.S. 199A.

*Mature bark color.*—Greyed-green R.H.S. 197A.

Branches: Current season branches are stiff, smooth barked, gradually upsweeping in orientation. Growth on tips of branches and leader stops early and abruptly, with terminal buds pointed in an upward direction, as opposed to the weeping tips generally seen on seedlings of the species in summer. Internodal length is quite short, 2 to 4 cm. on vigorously growing trees.

*Immature twig color.*—Yellow-green R.H.S. 153B.

*Mature twig color.*—Grey-brown R.H.S. 199A.

Leaves: Alternate, simple, entire, cordate.

*Margin.*—Leaf margin undulate and serrate.

*Tip.*—Acute to short acuminate.

*Leaf surface.*—Upper surface is slightly rugose between veins, glabrous. Under surface is glabrous except for small tufts of pubescence in axils of main veins.

*Leaf color.*—Upper summer leaf color is green R.H.S. 137A to yellow green R.H.S. 147A, with the under color being green R.H.S. 137C. The fall color is yellow R.H.S. 13A to yellow-orange R.H.S. 14B.

*Size.*—5–7 cm by 5–7 cm (excluding petioles). Unusually small when compared to typical *Tilia cordata* leaves.

*Stipules.*—None.

*Petioles.*—Short, stout. Size: 20–30 mm long by 1–2 mm thick. Color: Yellow-green R.H.S. 150C to R.H.S. 150D with the upper surface tinted red R.H.S. 42D where exposed to full sun.

Vegetative buds: Small, rounded, 3 mm by 3 mm average size, enclosed by three overlapping scales. Color of mature buds: greyed-red R.H.S. 178A.

Flowers: Tree has not been observed flowering as original plant has not yet reached flowering age.

Fruit: No fruit has been observed as the tree has not yet flowered nor produced fruit.

Growth rate: Very slow, dwarf tree.

Distinguishing Characteristics

Figure 1:
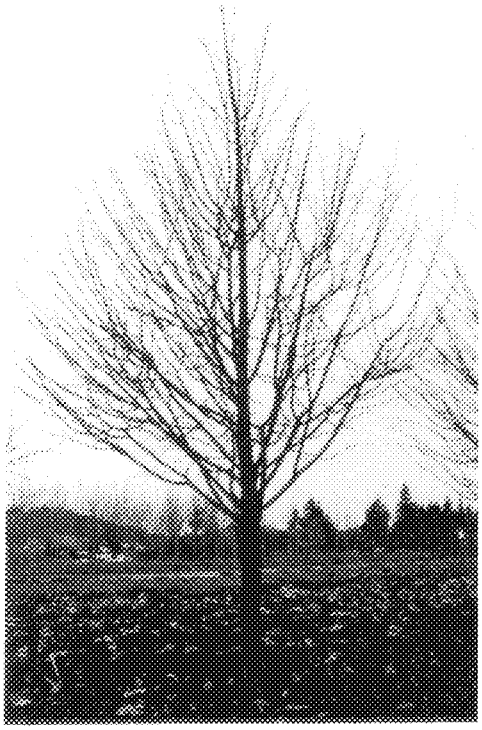
FIG. 1 is a photograph of a tree of my new variety in winter with its leaves shed to illustrate the compact conical shape of the tree.
Figure 2:
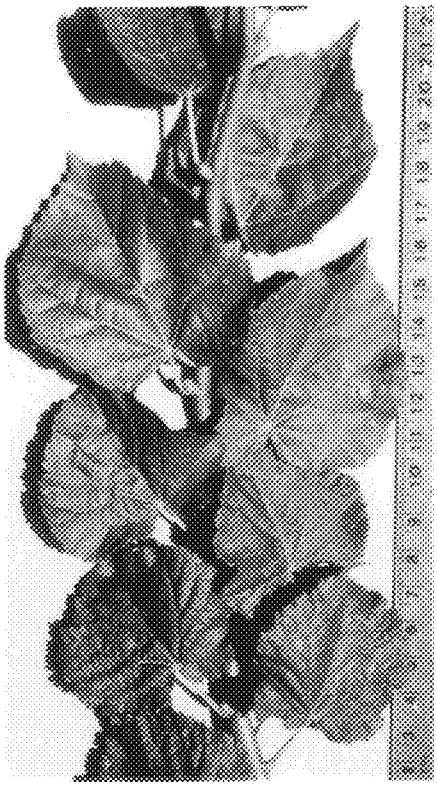
FIG. 2 is a photograph of a branch of a tree of my new variety.
Figure 3:
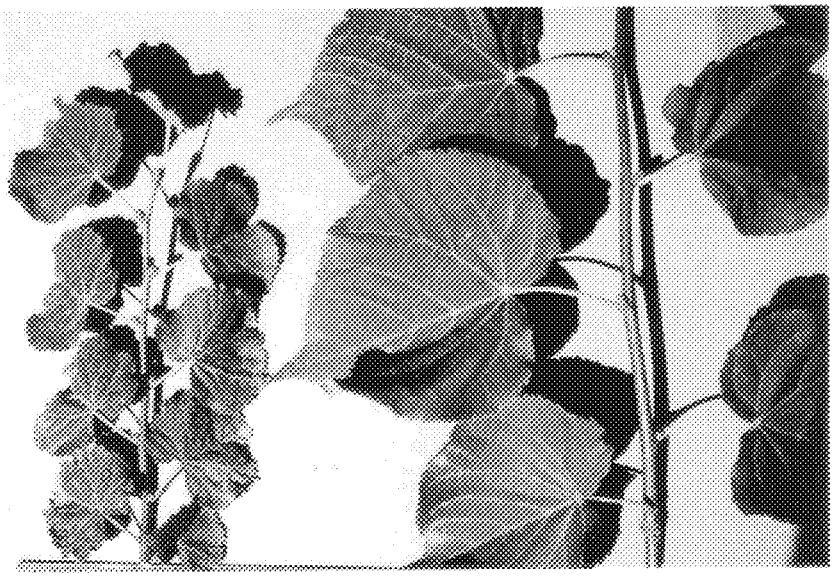
FIG. 3 is a comparison photograph of leaves on a branch of my new variety with leaves on seedling *Tilia cordata* growing under the same growing conditions.

My new variety is of a dwarf size and has an extremely compact growth and dense conical habit. The dwarf size has been evidenced as of this time by a growth rate that is half or less of that of the species growing under similar growing conditions and by a leaf size which is approximately one-half that of the species. The density and compact nature of the tree is evidenced by the extremely short internodal length of 2–4 cm which is between one-half and one-third that of the species observations to date. The conical shape of my new tree is evidenced by the symmetrically angled crown shape as shown in FIG. 1.

Observations

As reported in the table below, measurements were taken of ten one-year old trees of my new variety in a nursery in Boring, Oreg. to determine their average height. In addition, ten seedling *Tilia cordata* trees growing next to them in the nursery were also measured and averaged for height. The height was also measured and averaged for two nine year old trees of my new variety growing next to two typical seedlings of *Tilia cordata* trees of the same age. In addition, leaf size, branch length and internodal length was measured and averaged from ten three-year old trees of my new variety and compared with similar averaged measurements taken from ten seedling *Tilia cordata* trees of the same age, growing in the same row in the nursery.

The results of these observations are set forth in the table below.

| | New Cultivar | Seedling |
|---|---|---|
| 1 year old tree height | 61.3 cm. | 113.3 cm. |
| 9 year old tree height | 3.1 meters | 6.1 meters |
| Leaf length | 5.7 cm. | 12.9 cm. |
| Leaf width | 6.3 cm. | 12.2 cm. |
| Internode length | 3.2 cm. | 8.2 cm. |
| Branch length, one season's growth (on 3 yr. old trees) | 45.4 cm. | 112.5 cm. |

I claim:

1. A new and distinct variety of linden tree substantially as herein shown and described, characterized particularly as to novelty by a dwarf size, compact growth, and dense conical habit.

* * * * *